(12) United States Patent
Otoo

(10) Patent No.: US 12,037,353 B2
(45) Date of Patent: Jul. 16, 2024

(54) CARBON CAPTURE, STORAGE, AND RECYCLING COMPOSITIONS

(71) Applicant: OAKLAND CITY UNIVERSITY, FOUNDED BY GENERAL BAPTISTS, INC., Oakland City, IN (US)

(72) Inventor: Barnabas Otoo, Oakland City, IN (US)

(73) Assignee: OAKLAND CITY UNIVERSITY, FOUNDED BY GENERAL BAPTISTS, INC., Oakland City, IN (US)

( * ) Notice: Subject to any disclaimer, the term of this patent is extended or adjusted under 35 U.S.C. 154(b) by 47 days.

(21) Appl. No.: 17/861,740

(22) Filed: Jul. 11, 2022

(65) Prior Publication Data
US 2022/0348598 A1 Nov. 3, 2022

Related U.S. Application Data

(63) Continuation of application No. 17/289,441, filed as application No. PCT/US2019/057361 on Oct. 22, 2019, now Pat. No. 11,414,445.

(60) Provisional application No. 62/751,770, filed on Oct. 29, 2018.

(51) Int. Cl.
*C07C 51/00* (2006.01)
*C07F 9/6574* (2006.01)
(52) U.S. Cl.
CPC ............ *C07F 9/6574* (2013.01); *C07C 51/00* (2013.01)

(58) Field of Classification Search
CPC ...................................................... C07C 51/00
See application file for complete search history.

(56) References Cited

U.S. PATENT DOCUMENTS 3,520,849 A  7/1970 Vandenberg
2013/0053602 A1  2/2013 Madson

FOREIGN PATENT DOCUMENTS

CN  104291299  1/2015
WO  2016024293  2/2016

OTHER PUBLICATIONS

International Search Report and Written Opinion for PCT/US2019/057361 dated Jan. 14, 2020.
Zhao Y. et al., "Thermodynamic Properties of CO2 Conversion of Sodium Borohydride" Chemical Engineering & Technology, 2015, vol. 38, Issue 1, pp. 110-116; DOI: 10.1002/ceat.201400292; pp. 110-116.

*Primary Examiner* — Laura L Stockton
(74) *Attorney, Agent, or Firm* — Barnes & Thornburg LLP

(57) ABSTRACT

The invention relates to carbon dioxide dioxaphosphetane compositions, including solid carbon dioxide dioxaphosphetane compositions. The invention includes compositions and methods for the capture, storage, and recycling of carbon, including methods of boric acid catalyzed reduction of carbonates in aqueous media and the use of phosphate solutions for capture and recycling of carbon.

14 Claims, 19 Drawing Sheets

CARBON CAPTURE, STORAGE, AND RECYCLING COMPOSITIONS

CROSS-REFERENCE TO RELATED APPLICATION

This application is a continuation application of U.S. patent application Ser. No. 17/289,441, filed on Apr. 28, 2021, which is a U.S. national stage application under 35 U.S.C. § 371(b) of International Application No. PCT/US2019/057361 filed Oct. 22, 2019, which claims priority to the U.S. Patent Application No. 62/751,770 filed on Oct. 29, 2018, the disclosures of all which are hereby expressly incorporated by reference in their entirety.

TECHNICAL FIELD

The invention relates to solid carbon dioxide dioxaphosphetane compositions. The invention includes compositions and methods for the capture, storage, and recycling of carbon, including methods of boric acid catalyzed reduction of carbonates in aqueous media and the use of phosphate solutions for capture and recycling.

BACKGROUND AND SUMMARY OF THE INVENTION

Increasing global temperatures has led to an increased drive by governments and global organizations to control carbon levels in earth's atmosphere. Holistic control of atmospheric carbon as envisaged could be approached by various means, including energy efficiency and preservation, increased investment in renewable energy, afforestation, and post combustion carbon capture. Among these, post combustion carbon capture and recycling has great appeal to existing industries as it only requires fitting already existing exhaust systems with procedures to remove and recycle $CO_2$ that is produced.

Current procedures for post combustion carbon capture encompass flushing flue gas through amines that selectively capture the $CO_2$ then later separating the $CO_2$. The use of metal oxides, various nanomaterials, and other chemicals for carbon capture have been investigated. Triphenylphosphine has also been utilized to capture $CO_2$ in combination with other chemicals. However, these procedures are typically cost intensive, prompting scientists to look for efficient, less expensive methods.

The recycling of captured carbon has also been an area of great concern and scientific activity. Advantageous processes must be cost effective and energy efficient. Many methods have been proposed for the recycling of captured carbon. One such method is the reduction of carbonates using metal hydrides. Although lithium aluminum hydride procedures strictly require non-aqueous media, sodium borohydride procedures in aqueous media can only achieve partial reduction of bicarbonates but not carbonates. Thus, there exists a need for alternative means for carbon capture, storage and recycling.

Recent investigation of the combination of water-soluble carbonyls (aldehydes and ketones) with inorganic phosphates to form dioxaphosphetanes has been expanded in the present disclosure to include carbon dioxide. As a result, the present disclosure provides a simple and less expensive approach to carbon capture, storage and recycling.

The solid carbon dioxide dioxaphosphetane compositions and the carbonate recycling methods provided in the present disclosure provide advantages compared to similar compositions known in the art. For instance, the solid dioxaphosphetanes can be stored at room temperature for extended periods of time without noticeable change in composition. Likewise, dioxaphosphetane solutions can be stored in closed containers at room temperature for extended periods of time without noticeable change in composition. Furthermore, the solid dioxaphosphetanes can be maintained without release of $CO_2$ at appropriate pH values, for instance a pH of 7 or above. Moreover, synthesis of ammonium and potassium-$CO_2$ dioxaphophetanes, and dialkylphosphate dioxaphosphetanes, have also be achieved. Insoluble dioxaphosphetanes of calcium, copper, zinc and other non-alkali metals can be precipitated when the metal chloride/nitrate solutions are added to the solution of sodium dioxaphosphetane.

The present disclosure provides compositions and methods to achieve the reduction of $CO_2$ to formic acid both indirectly as carbonates and directly as flue gas, which can be utilized as a first step in the recycling of $CO_2$. Indirect reduction of $CO_2$ by reducing sodium bicarbonate in the presence of phosphates also disclosed. This methodology can also be utilized as an option for carbon transportation. Coincidentally, Formica ants, stingless bees and the stingless nettle, organisms that are naturally associated with formic acid, have also been linked with phosphate rich habitats.

The following numbered embodiments are contemplated and are non-limiting:

1. A solid carbon dioxide dioxaphosphetane composition having the chemical structure

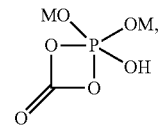

wherein M is a cation and/or an alkyl group.

2. The solid carbon dioxide dioxaphosphetane composition of clause 1, wherein M is selected from the group consisting of H, Na, K, aryl, and alkyl.
3. The solid carbon dioxide dioxaphosphetane composition of clause 1 or clause 2, wherein the composition is crystalline.
4. The solid carbon dioxide dioxaphosphetane composition of any one of clauses 1 to 3, wherein the composition is at a pH of 7 or greater.
5. A process for making a carbon dioxide dioxaphosphetane composition, said process comprising the steps of:
   a. combining a phosphate and water in a container;
   b. flushing the combination of dibasic sodium phosphate and water with carbon dioxide;
   c. stirring the resultant combination; and
   d. cooling the resultant combination to form the carbon dioxide dioxaphosphetane composition.
6. The process of clause 5, wherein the phosphate is selected from the group consisting of ammonium phosphate, sodium phosphate, potassium phosphate, and dialkyl phosphate.
7. The process of clause 5 or clause 6, wherein the carbon dioxide dioxaphosphetane composition is a crystalline composition.
8. The process of clause 5 or clause 6, wherein the stirring is for about 2 hours.
9. The process of clause 5 or clause 6, wherein the stirring is for between 2 hours and 8 hours.

10. The process of clause 5 or clause 6, wherein the stirring is for between 2 hours and 12 hours.
11. The process of clause 5 or clause 6, wherein the stirring is for between 12 and 48 hours.
12. The process of clause 5 or clause 6, wherein the stirring is for at least 12 hours.
13. The process of any one of clauses 5 to 12, wherein the cooling is in an ice water bath.
14. A product formed by the process of clause 5.
15. A method of reducing carbon dioxide, said method comprising the steps of:
    a. obtaining a carbon dioxide dioxaphosphetane composition;
    b. placing the carbon dioxide dioxaphosphetane composition in a solution; and
    c. combining sodium borohydride with the solution comprising carbon dioxide dioxaphosphetane to form a formate composition and reduce carbon dioxide.
16. The method of clause 15, wherein the formate composition is sodium formate.
17. The method of clause 15 or clause 16, wherein phosphate is precipitated via combination of sodium borohydride with the solution comprising carbon dioxide dioxaphosphetane.
18. The method of any one of clauses 15 to 17, wherein the method is utilized to transport carbon.
19. The method of any one of clauses 15 to 17, wherein the method is utilized to recycle carbon.
20. A process for reducing a carbonate, said process comprising the steps of:
    a. dissolving the carbonate in water;
    b. combining the carbonate solution of step a) with boric acid;
    c. adding sodium borohydride to the combination of step b) to reduce the carbonate to a formate.
21. The process of clause 20, wherein the process further comprises the step of stirring the combination of step b).
22. The process of clause 20 or clause 21, wherein the process is performed at room temperature.
23. The process of any one of clauses 20 to 22, wherein the carbonate is a water-soluble carbonate.
24. The process of any one of clauses 20 to 23, wherein the carbonate is a metal carbonate.
25. The process of clause 24, wherein the metal carbonate is selected from the group consisting of an ammonium carbonate, a sodium carbonate, a potassium carbonate, a rubidium carbonate, and a cesium carbonate.
26. The process of clause 24, wherein the metal carbonate is an alkali metal carbonate.
27. The process of clause 24, wherein the metal carbonate is a sodium carbonate.
28. The process of any one of clauses 20 to 23, wherein the carbonate is a bicarbonate.
29. The process of clause 28, wherein the bicarbonate is a sodium bicarbonate.
30. The process of any one of clauses 20 to 29, wherein the formate is a sodium formate.
31. The process of any one of clauses 20 to 30, wherein the boric acid is added in step b) at about 1 molar equivalent of boric acid to carbonate.
32. The process of any one of clauses 20 to 30, wherein the boric acid is added in step b) at more than 1 molar equivalent of boric acid to carbonate.
33. The process of any one of clauses 20 to 32, wherein the carbonate is reduced to a formate at an efficacy of at least 90%.
34. The process of any one of clauses 20 to 32, wherein the carbonate is reduced to a formate at an efficacy of about 90%.
35. The process of any one of clauses 20 to 32, wherein the carbonate is reduced to a formate at an efficacy of about 95%.
36. The process of any one of clauses 20 to 32, wherein the carbonate is reduced to a formate at an efficacy between 90-100%.
37. A method of capturing carbon dioxide, said method comprising the step of capturing carbon dioxide in a carbon dioxide dioxaphosphetane composition having the chemical structure $$\begin{array}{c} MO \diagdown \diagup OM, \\ O-P \\ \diagdown \diagup \diagdown OH \\ O \\ \| \\ O \end{array}$$

wherein M is a cation and/or alkyl groups, and wherein the carbon dioxide dioxaphosphetane composition is an aqueous phosphate solution.
38. The method of clause 37, wherein M is selected from the group consisting of H, Na, K, aryl, and alkyl.
39. The method of clause 37 or clause 38, wherein the phosphate is selected from the group consisting of ammonium phosphate, sodium phosphate, potassium phosphate, and dialkyl phosphate.
40. A process for making a carbon dioxide dioxaphosphetane composition, said process comprising the steps of:
    a. combining a phosphate and water in a container;
    b. flushing the combination of step a) with carbon dioxide; and
    c stirring the combination.
41. The process of clause 40, further comprising the step of storing the combination.
42. The process of clause 40 or clause 41, wherein the phosphate is selected from the group consisting of ammonium phosphate, sodium phosphate, potassium phosphate, and dialkyl phosphate.
43. The process of any one of clauses 40 to 42, wherein the stirring is for about 2 hours.
44. The process of any one of clauses 40 to 42, wherein the stirring is for between 2 hours and 8 hours.
45. The process of any one of clauses 40 to 42, wherein the stirring is for between 2 hours and 12 hours.
46. The process of any one of clauses 40 to 42, wherein the stirring is for between 12 and 48 hours.
47. The process of any one of clauses 40 to 42, wherein the stirring is for at least 12 hours.
48. A product formed by the process of clause 40.
49. A method of reducing carbon dioxide, said method comprising the step of combining sodium borohydride with a carbon dioxide dioxaphosphetane solution to form a formate.

Figure 1:
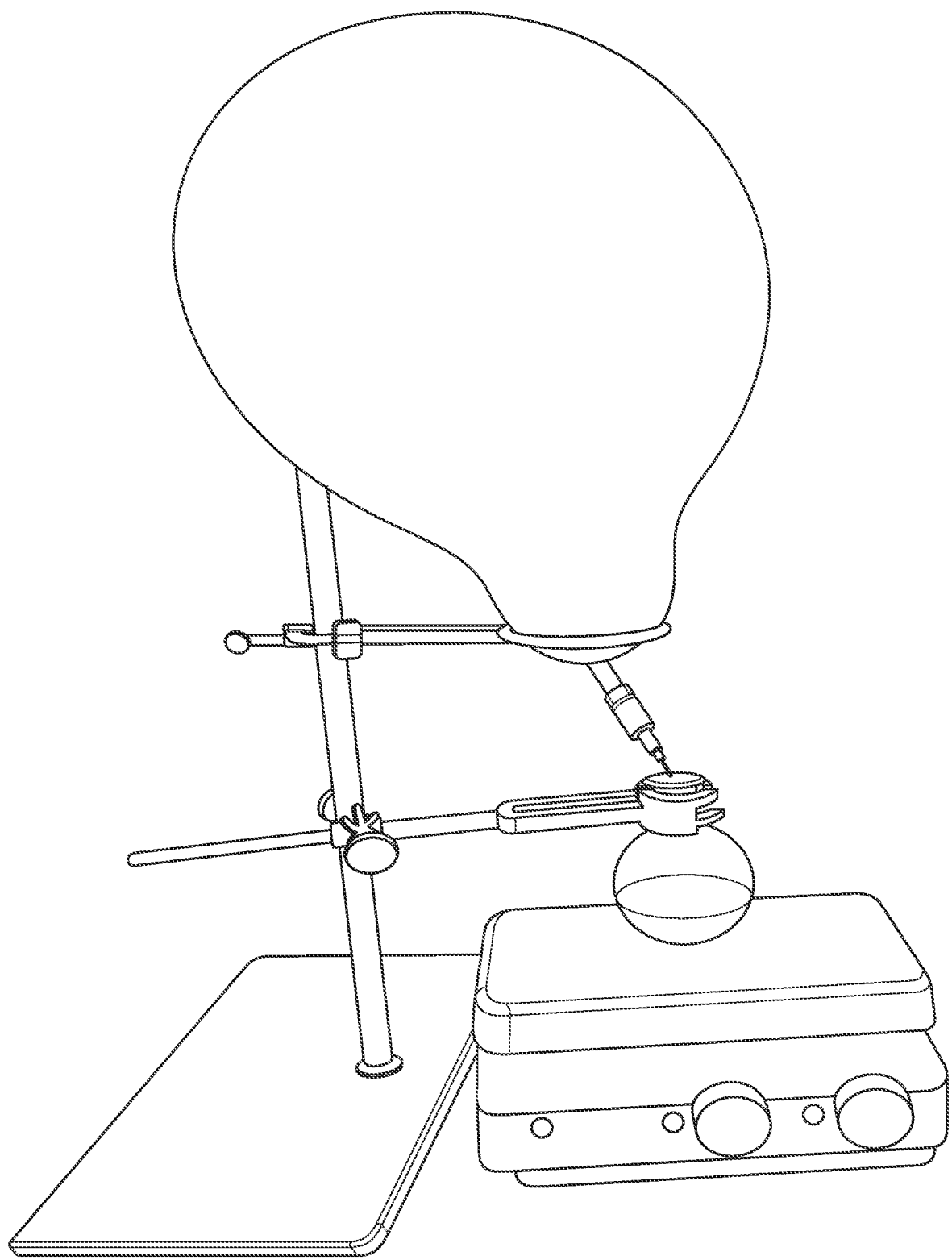
FIG. 1 shows an apparatus for capture of $CO_2$ using food grade $CO_2$.

Various embodiments of the invention are described herein as follows. In certain aspects described herein, a solid carbon dioxide dioxaphosphetane composition is provided. The solid carbon dioxide dioxaphosphetane composition has the chemical structure

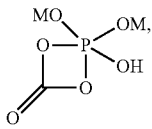

wherein M is a cation and/or an alkyl group. In some embodiments, M is selected from the group consisting of H, Na, K, aryl, and alkyl. In various embodiments, the composition is crystalline. In certain aspects, the composition is at a pH of 7 or greater. In one embodiment, the solid carbon dioxide dioxaphosphetane composition has the chemical structure

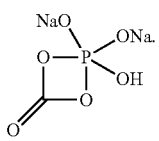

In other aspects, a process for making a carbon dioxide dioxaphosphetane composition is provided. The process comprises the steps of a) combining a phosphate and water in a container; b) flushing the combination of dibasic sodium phosphate and water with carbon dioxide; c) stirring the resultant combination; and d) cooling the resultant combination to form the carbon dioxide dioxaphosphetane composition. In some embodiments, the phosphate is selected from the group consisting of ammonium phosphate, sodium phosphate, potassium phosphate, and dialkyl phosphate. In other embodiments, the carbon dioxide dioxaphosphetane composition is a crystalline composition.

In some embodiments, the stirring is for about 2 hours. In other embodiments, the stirring is for between 2 hours and 8 hours. In yet other embodiments, the stirring is for between 2 hours and 12 hours. In some embodiments, the stirring is for between 12 and 48 hours. In other embodiments, the stirring is for at least 12 hours. In various embodiments, the cooling is in an ice water bath.

A product formed by the process is also provided.

In yet another aspect, a method of reducing carbon dioxide is provided. The method comprises the steps of a) obtaining a carbon dioxide dioxaphosphetane composition, b) placing the carbon dioxide dioxaphosphetane composition in a solution; and c) combining sodium borohydride with the solution comprising carbon dioxide dioxaphosphetane to form a formate composition and reduce carbon dioxide. In some embodiments, the formate composition is sodium formate. In other embodiments, phosphate is precipitated via combination of sodium borohydride with the solution comprising carbon dioxide dioxaphosphetane. In some aspects, the method is utilized to transport carbon. In other aspects, the method is utilized to recycle carbon.

A process for reducing a carbonate is also provided. The process comprises the steps of a) dissolving the carbonate in water; b) combining the carbonate solution of step a) with boric acid; and c) adding sodium borohydride to the combination of step b) to reduce the carbonate to a formate. In certain embodiments, the process further comprises the step of stirring the combination of step b). In some embodiments, the process is performed at room temperature. In other embodiments, the carbonate is a water-soluble carbonate. In yet other embodiments, the carbonate is a metal carbonate. In some embodiments, the metal carbonate is selected from the group consisting of an ammonium carbonate, a sodium carbonate, a potassium carbonate, a rubidium carbonate, and a cesium carbonate. In other embodiments, the metal carbonate is an alkali metal carbonate. In yet other embodiments, the metal carbonate is a sodium carbonate. In some embodiments, the carbonate is a bicarbonate. In other embodiments, the bicarbonate is a sodium bicarbonate. In yet other embodiments, the formate is a sodium formate. In some embodiments, the boric acid is added in step b) at about 1 molar equivalent of boric acid to carbonate. In other embodiments, the boric acid is added in step b) at more than 1 molar equivalent of boric acid to carbonate.

In yet other embodiments, the carbonate is reduced to a formate at an efficacy of at least 90%. In some embodiments, the carbonate is reduced to a formate at an efficacy of about 90%. In other embodiments, the carbonate is reduced to a formate at an efficacy of about 95%. In yet other embodiments, the carbonate is reduced to a formate at an efficacy between 90-100%.

In yet another aspect, a method of capturing carbon dioxide is provided. The method comprises the step of capturing carbon dioxide in a carbon dioxide dioxaphosphetane composition having the chemical structure

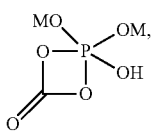

wherein M is a cation and/or alkyl groups, and wherein the carbon dioxide dioxaphosphetane composition is an aqueous phosphate solution. In some embodiments, M is selected from the group consisting of H, Na, K, aryl, and alkyl. In various embodiments, the phosphate is selected from the group consisting of ammonium phosphate, sodium phosphate, potassium phosphate, and dialkyl phosphate.

In another aspect, a process for making a carbon dioxide dioxaphosphetane composition is provided. The process comprises the steps of a) combining a phosphate and water in a container; b) flushing the combination of step a) with carbon dioxide; and c) stirring the combination. In some embodiments, the process further comprises the step of storing the combination. In various embodiments, the phosphate is selected from the group consisting of ammonium phosphate, sodium phosphate, potassium phosphate, and dialkyl phosphate.

In some embodiments, the stirring is for about 2 hours. In other embodiments, the stirring is for between 2 hours and 8 hours. In yet other embodiments, the stirring is for between 2 hours and 12 hours. In some embodiments, the stirring is for between 12 and 48 hours. In other embodiments, the stirring is for at least 12 hours.

A product formed by the process is also provided.

In one aspect, a method of reducing carbon dioxide is provided. The method comprises the step of combining sodium borohydride with a carbon dioxide dioxaphosphetane solution to form a formate.

Example 1

Formation of $CO_2$ Dioxaphosphetane Using Food Grade Carbon Dioxide

A 100 mL round bottom flask containing a stirring bar was charged with a 40 mL water and 2.84 g dibasic sodium phosphate to form a solution. The flask was fitted and sealed with a septum. The solution was flashed with food grade carbon dioxide (Airgas, Evansville, Indiana) according to the following protocol pursuant to Scheme 1:

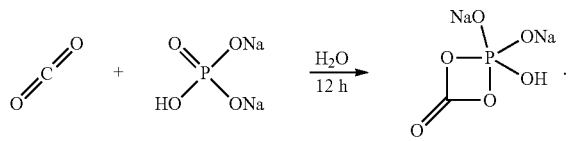

A long needle directly connected to the $CO_2$ tank was inserted through the septum such that the tip of the needle was close to the surface of the solution (see FIG. 1). A shorter needle was also pushed into the septum such that the tip was just inside the flask. The gas outlet on the $CO_2$ tank was opened while stirring the solution.

After a few minutes, the shorter needle was removed followed by the long needle with the gas tank still open. A balloon filled with $CO_2$ and taped unto a syringe and a needle was inserted into the septum to maintain an atmosphere of $CO_2$ in the flask. After 48 hours of stirring, the solution was cooled in an ice/water bath and filtered to produce the solid dioxaphosphetane in crystalline form.

Figure 2:
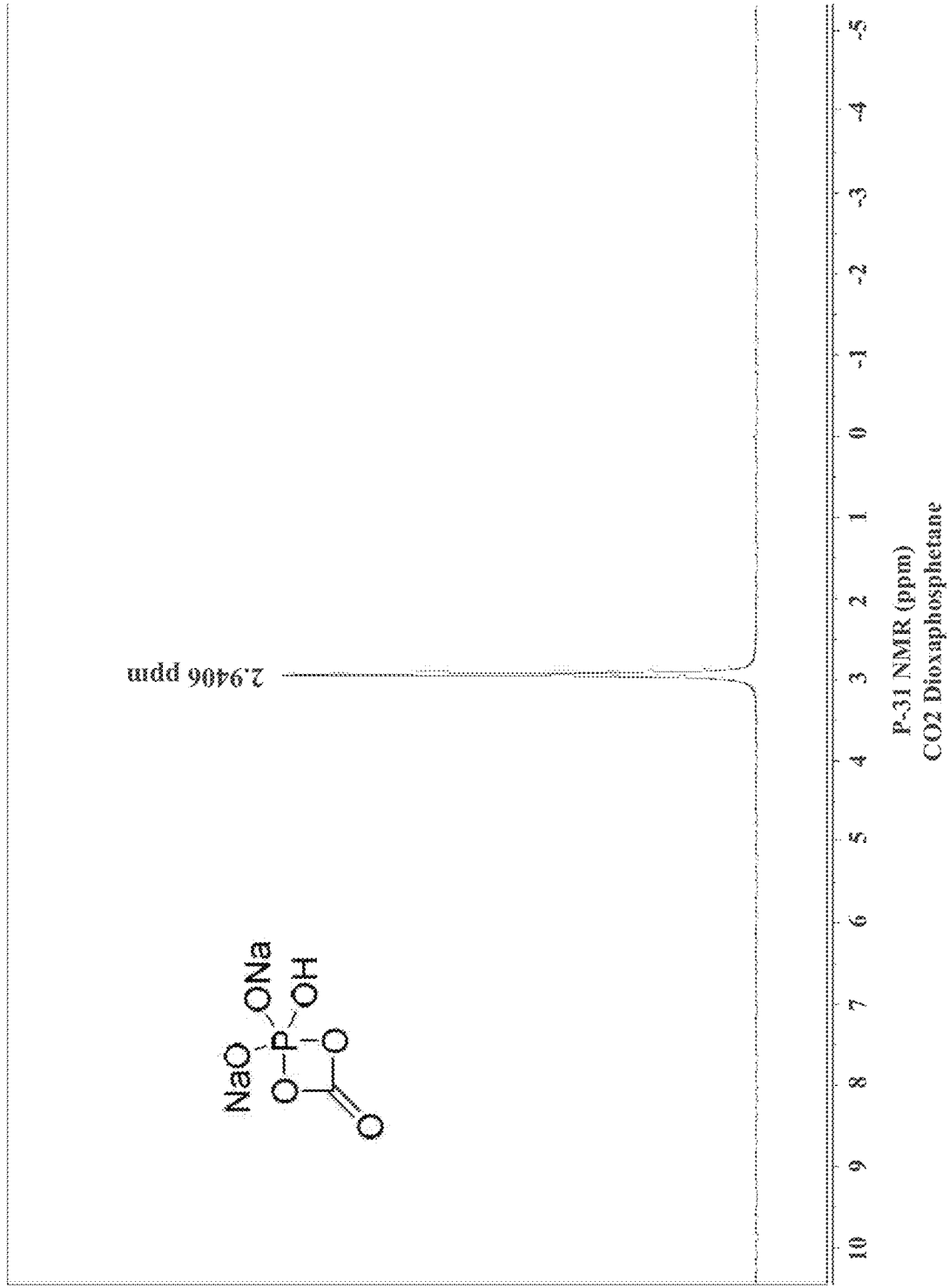
FIG. 2 shows $^{31}P$ nmr of dioxaphosphetane of $CO_2$.

The solid dioxaphosphetane in crystalline form was observed to have a $^{31}P$ nmr chemical shift of 2.9406 ppm (see FIG. 2). The chemical shift of $Na_2HPO_4$ of similar concentration taken before and after that of the dioxaphosphetane is 3.4311 ppm.

Figure 3:
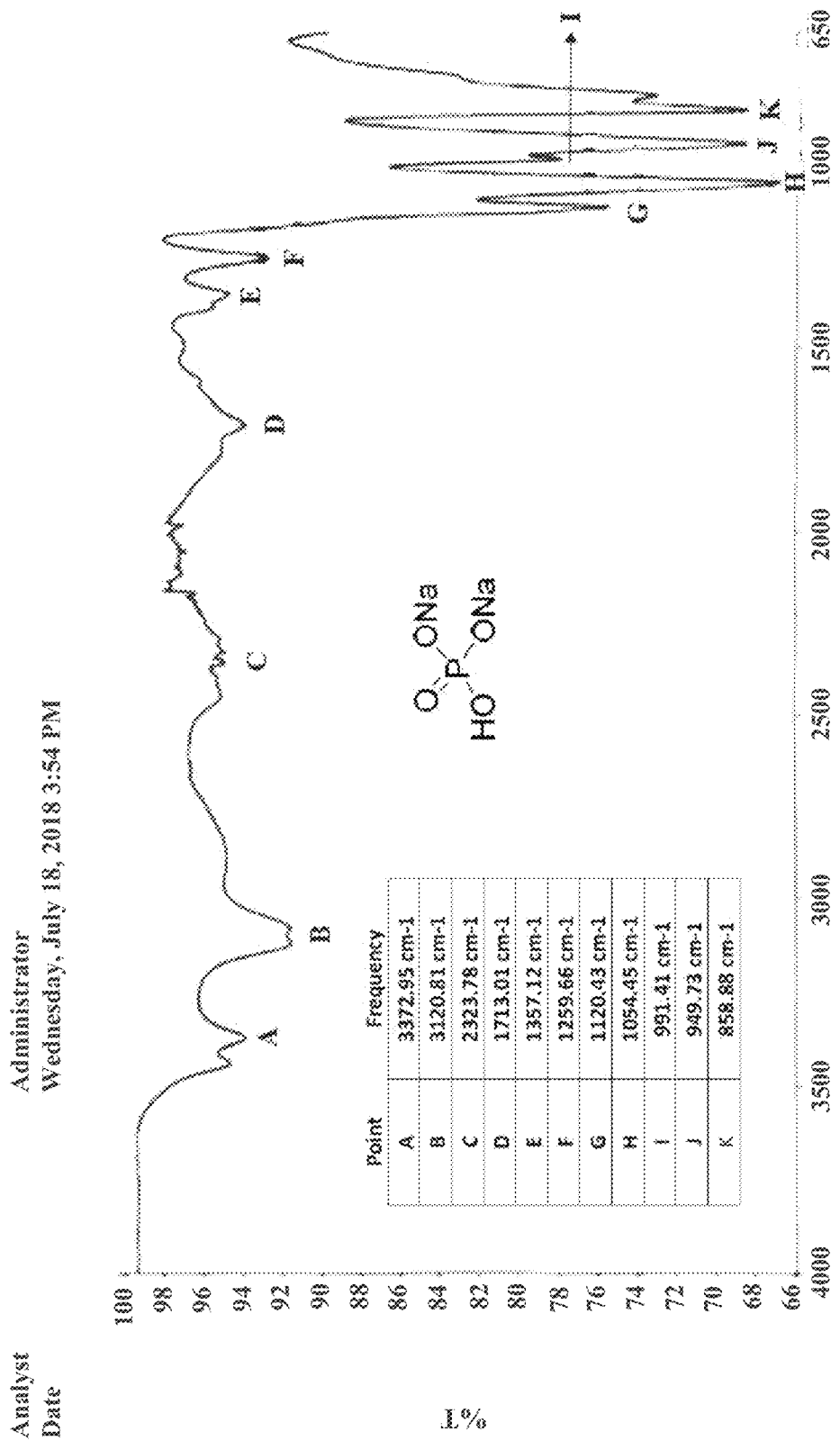
FIG. 3 shows FTIR of dibasic sodium phosphate.
Figure 4:
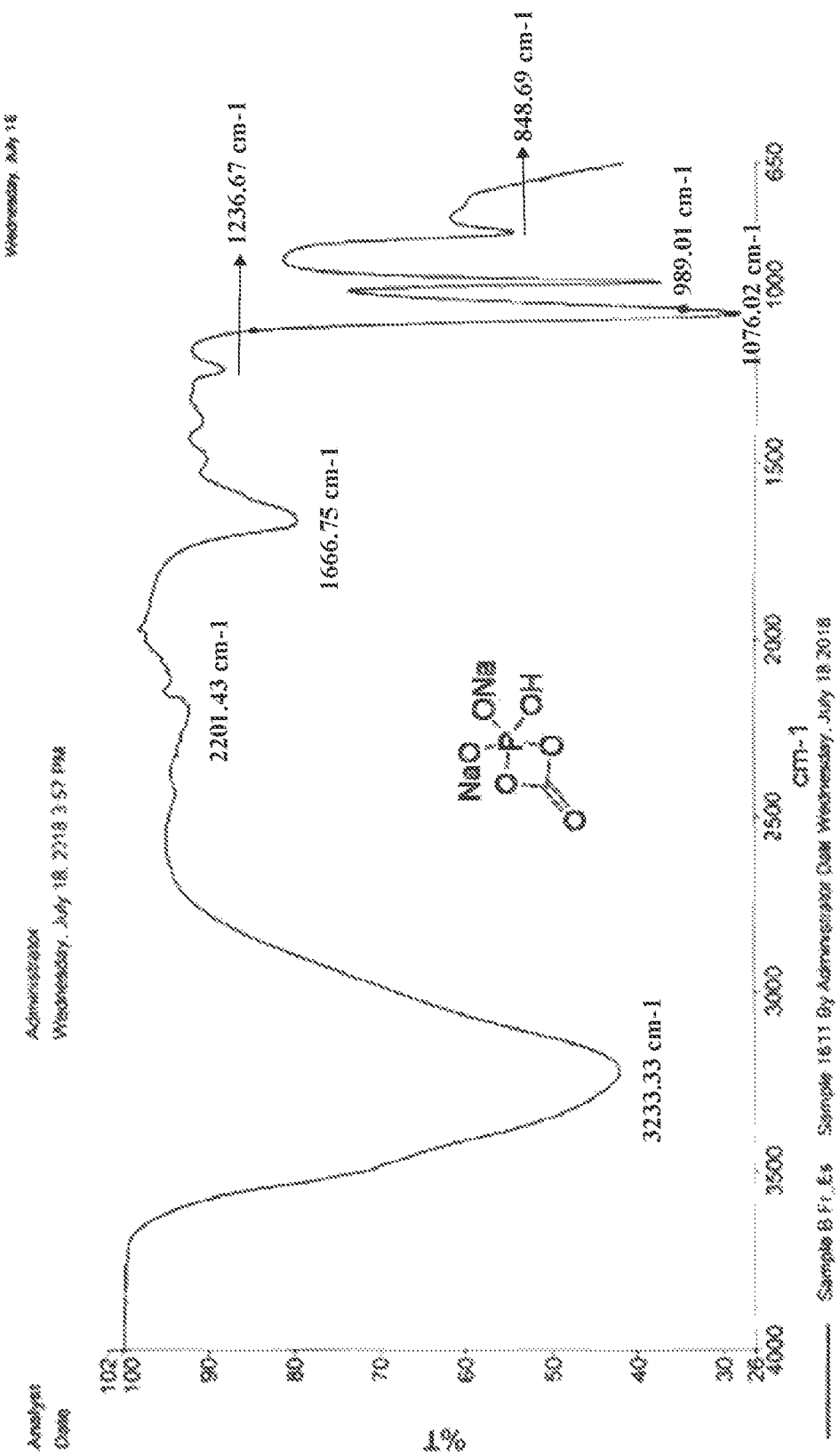
FIG. 4 shows FTIR of hydrated dioxaphosphetane of $CO_2$.

FTIR of the dioxaphosphetane reveal disappearance of the P=O frequency at 1120 $cm^{-1}$ and the appearance of a medium broad carbonyl peak at 1666.75 $cm^{-1}$ frequency (FIG. 3 and FIG. 4).

The instant example can also be reproduced to produce a solution of dioxaphosphetane.

Example 2

Figure 5:
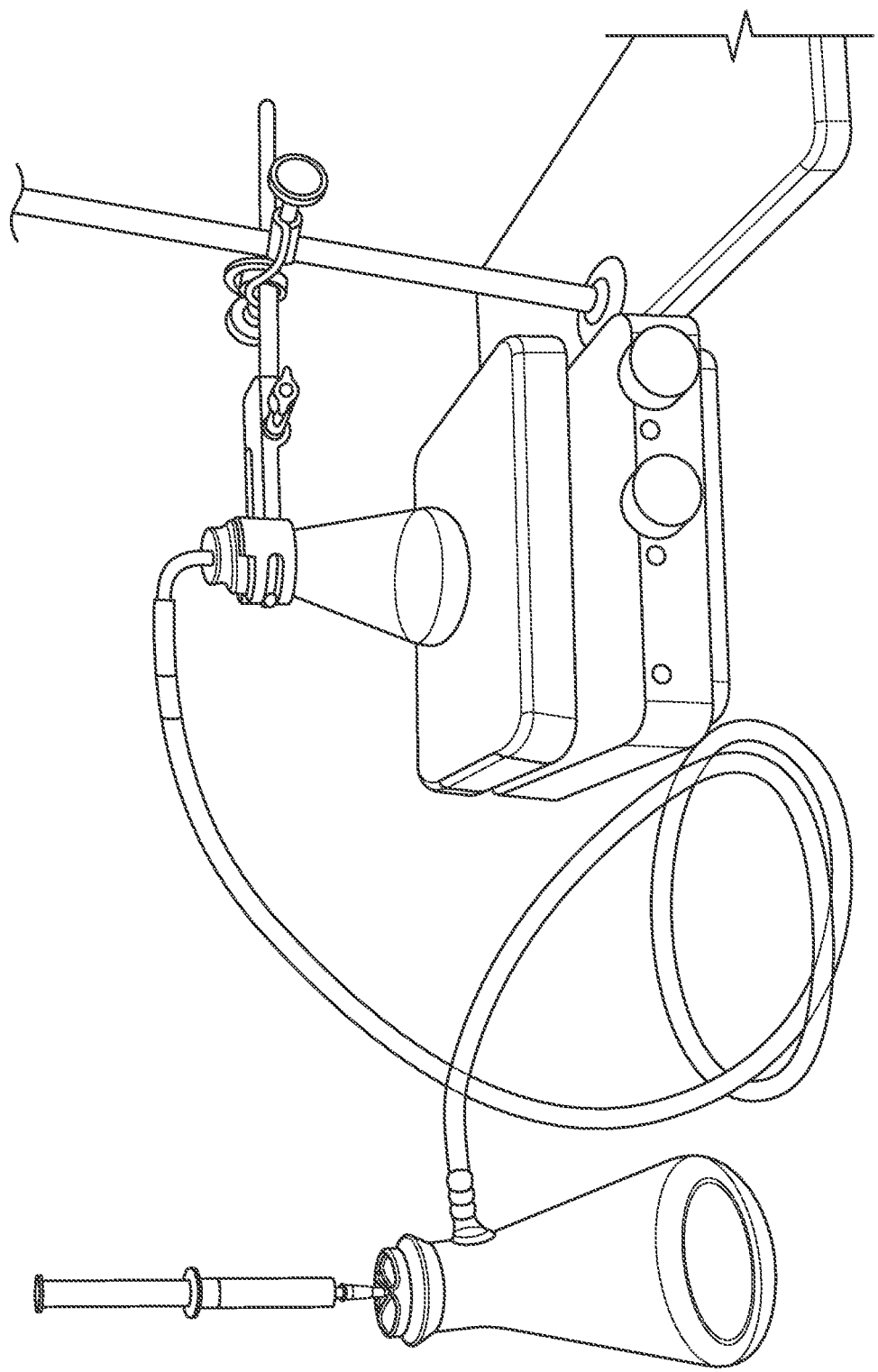
FIG. 5 shows an apparatus for capture of $CO_2$ from sodium carbonate.
Figure 6:
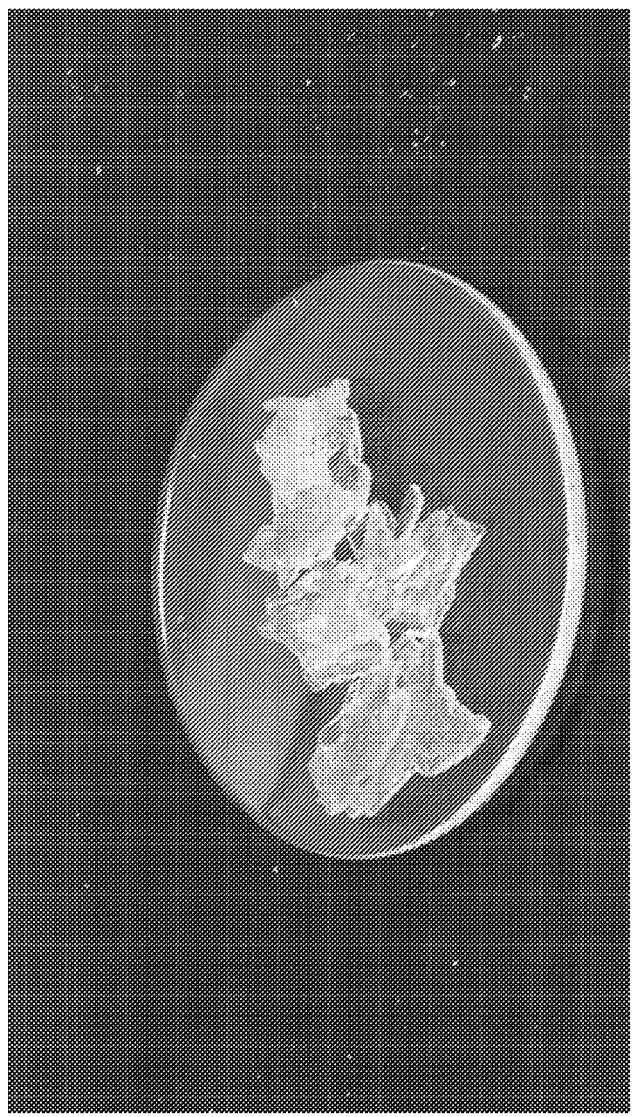
FIG. 6 shows $CO_2$ dioxaphosphetane in crystalline form.

Formation of Dioxaphosphetane Using Carbon Dioxide Generated from Sodium Carbonate The $CO_2$ receiving flask containing a 2.84 g of dibasic sodium phosphate dissolved in 40 mL deionized water was connected to the $CO_2$ generating flask containing 5 g of sodium carbonate (see FIG. 5). $CO_2$ was generated by injecting 10 mL of 4 M Hydrochloric acid into the generating flask. The solution in the receiving flask was stirred for 48 hours without dismantling the apparatus. The system was then dismantled and the receiving flask was cooled in an ice/water bath to produce dioxaphosphetane in crystalline form (see FIG. 6).

Example 3

Reduction of $CO_2$ to Formate

Addition of sodium borohydride to a solution of the dioxaphosphetane partially reduced it to formate. The remaining dioxaphosphetane was converted to sodium carbonate (Scheme 2).

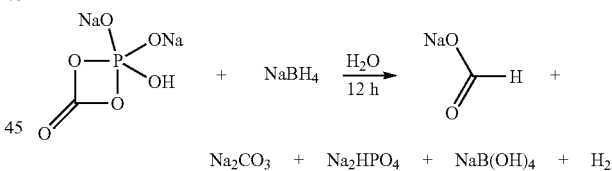

Dioxaphosphetanes generally activate the phosphorus atom for nucleophilic substitution. Nucleophilic attack of the hydrides on the phosphorus produced the carbonate with a CNMR chemical shift of 163.7.

Figure 7:
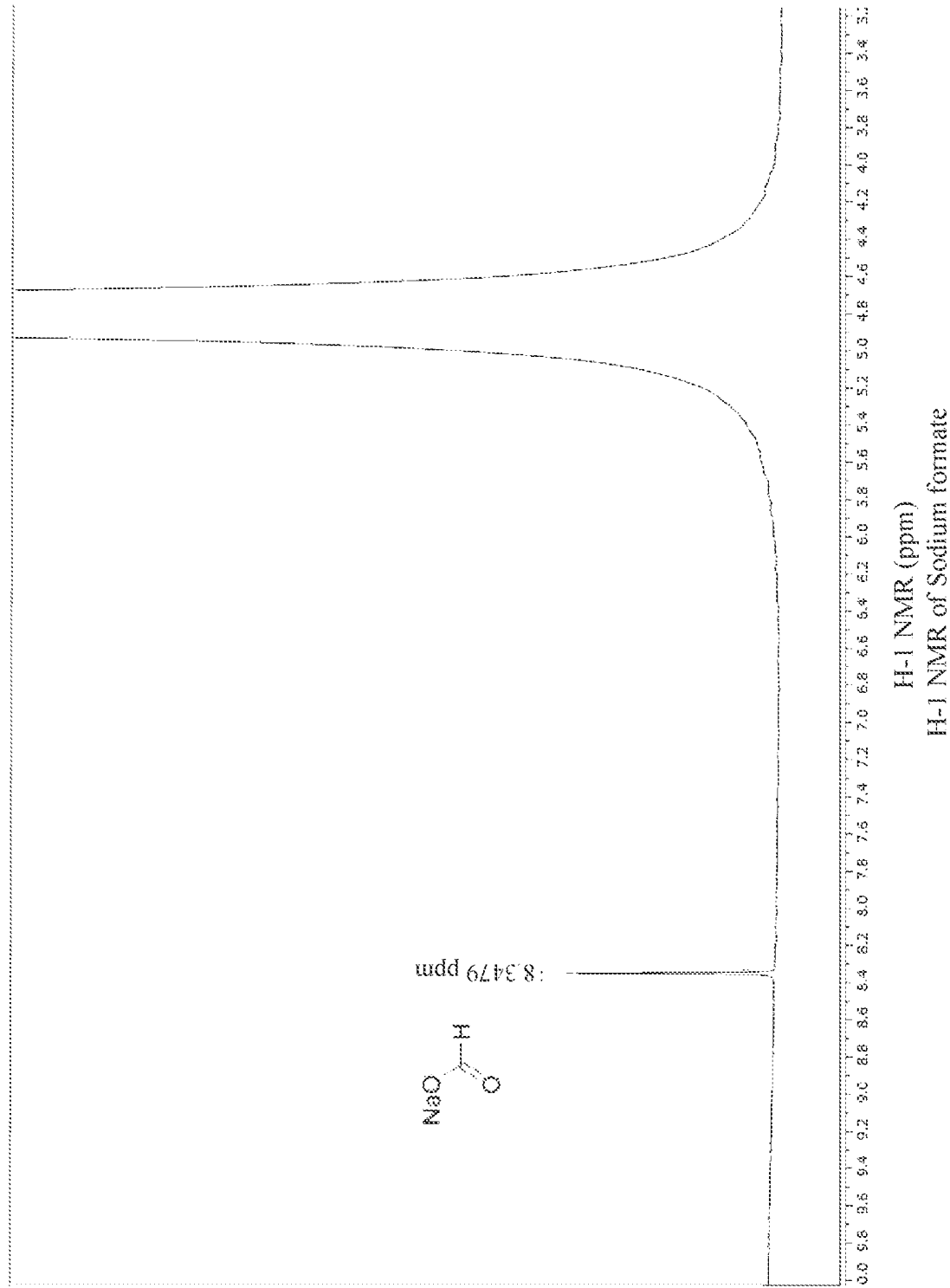
FIG. 7 shows $^1H$ nmr of sodium formate from reduction taken in D2O.
Figure 8:
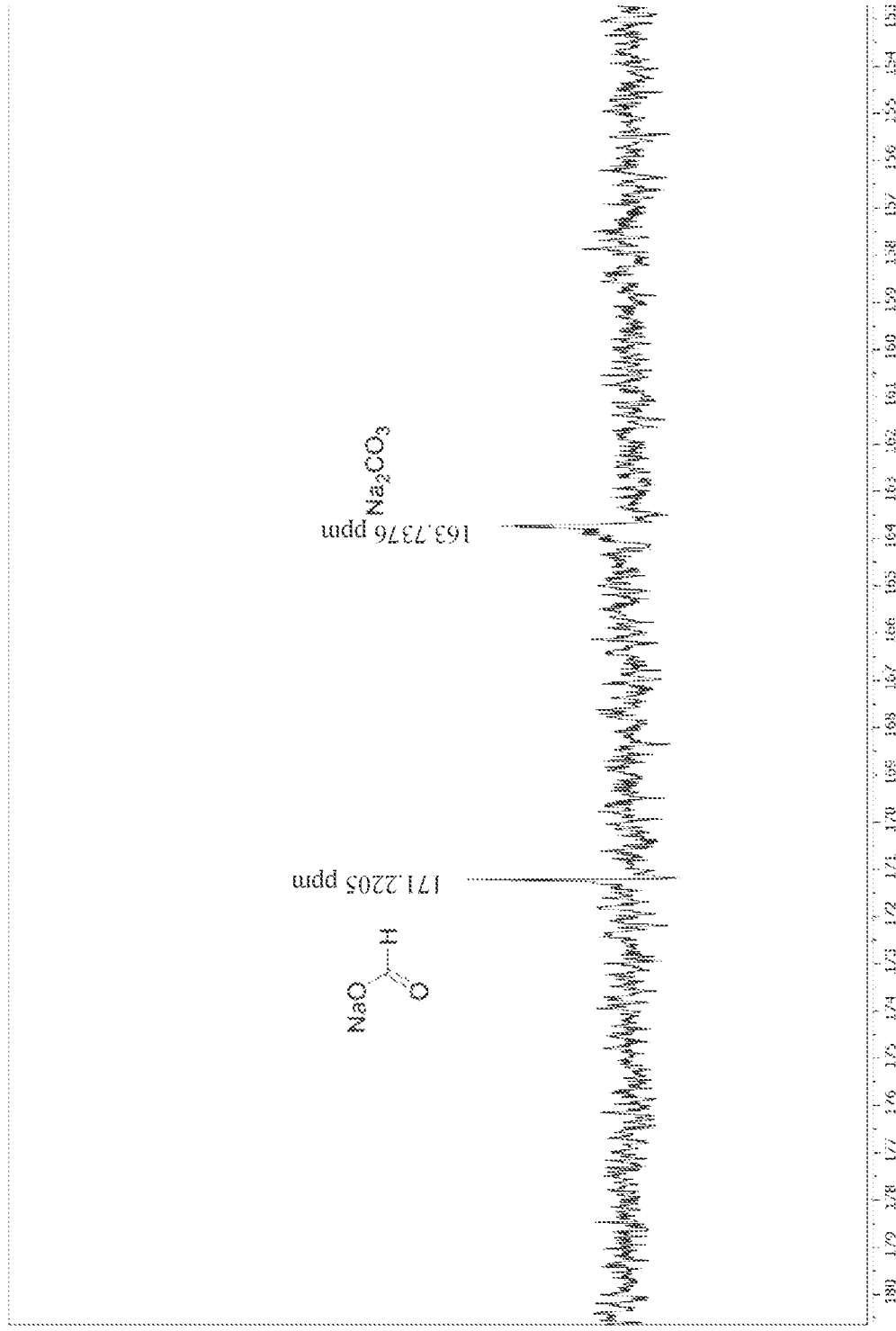
FIG. 8 shows $^{13}C$ nmr of reduction of dioxaphosphetane to form sodium formate and sodium bicarbonate.
Figure 9:
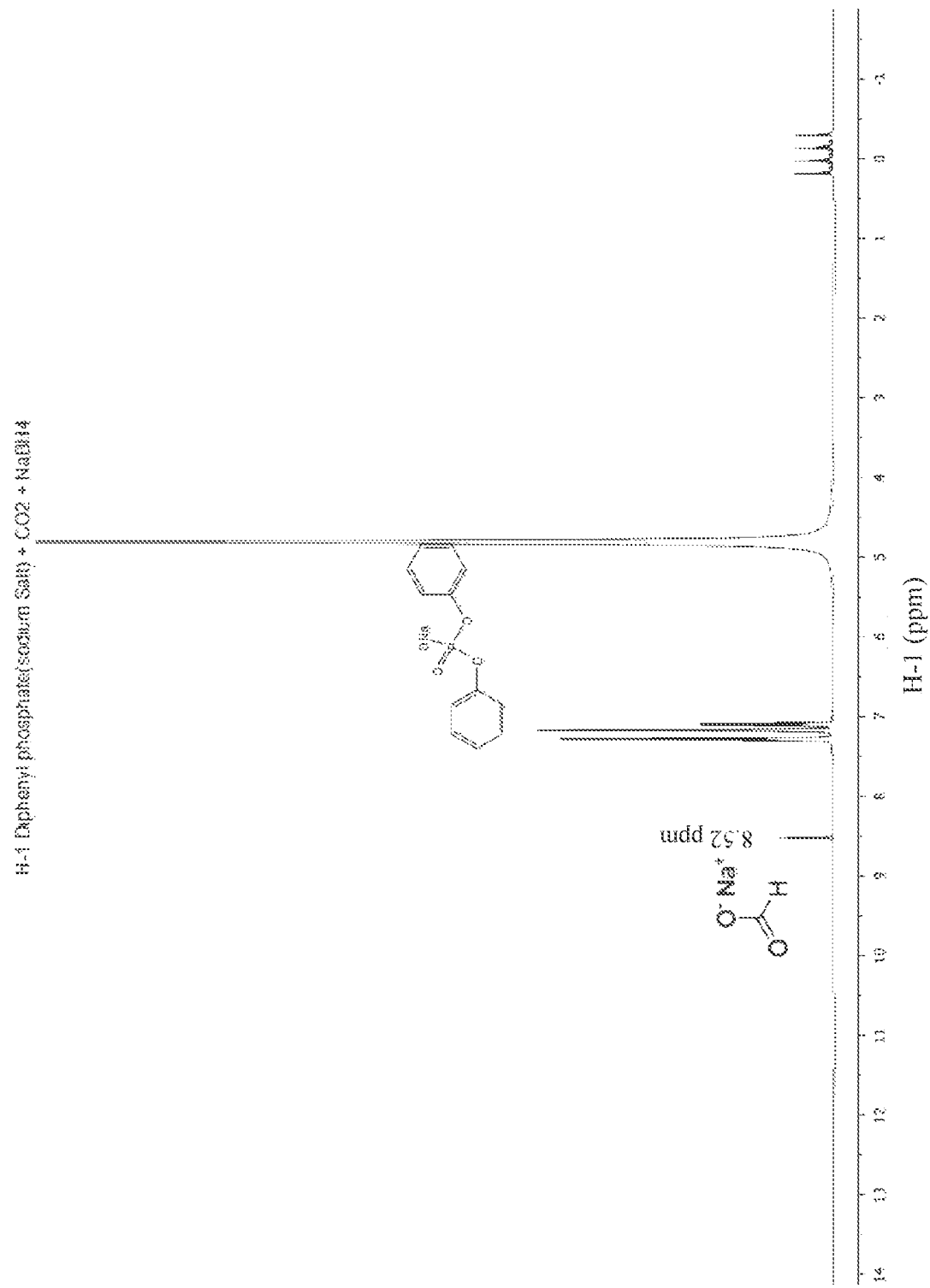
FIG. 9 shows $^1H$ nmr of diphenyl phosphate (sodium salt)+CO2+NaBH4.
Figure 10:
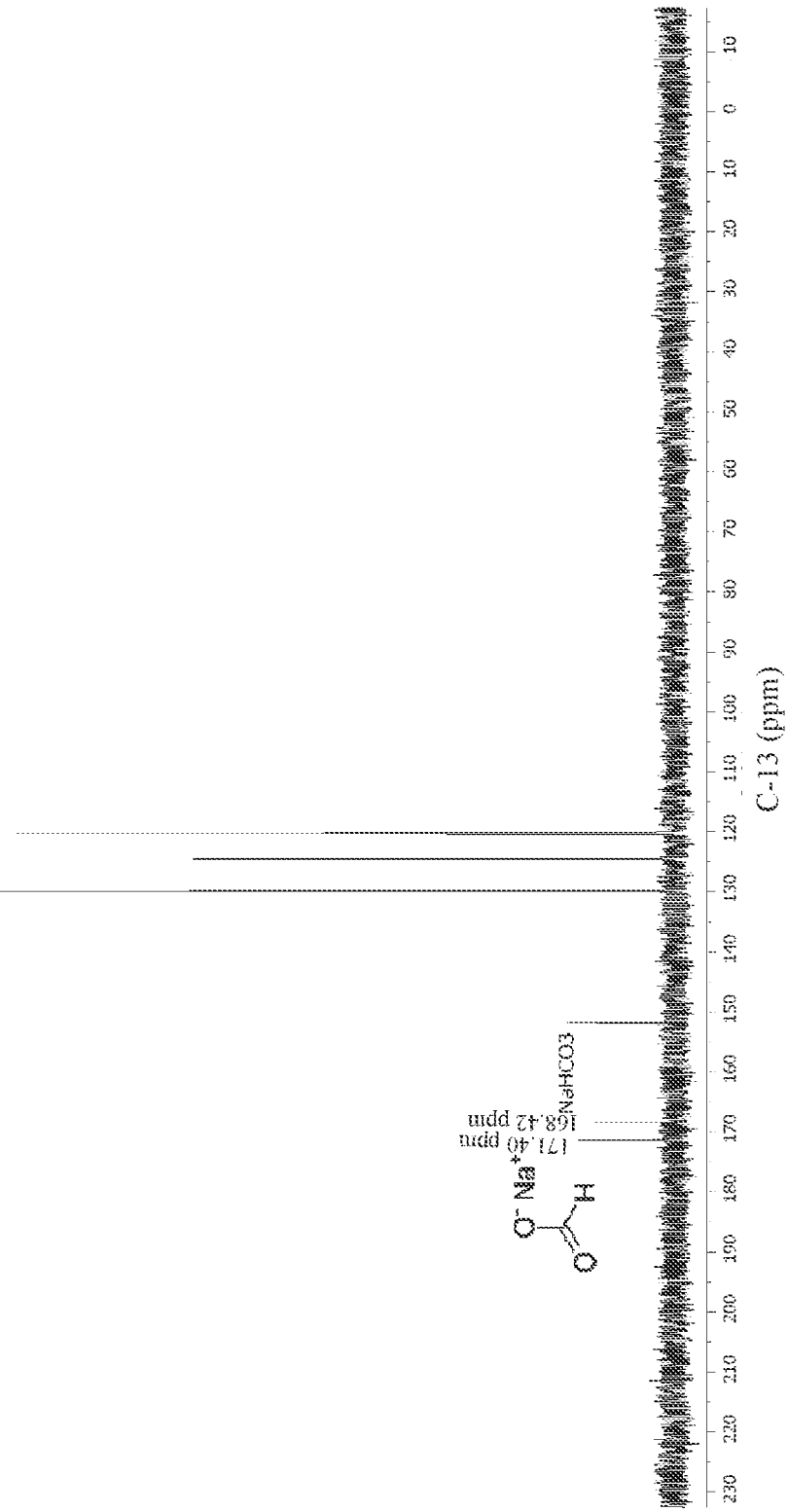
FIG. 10 shows $^{13}C$ nmr of diphenyl phosphate (sodium salt)+CO2+NaBH4.
Figure 11:
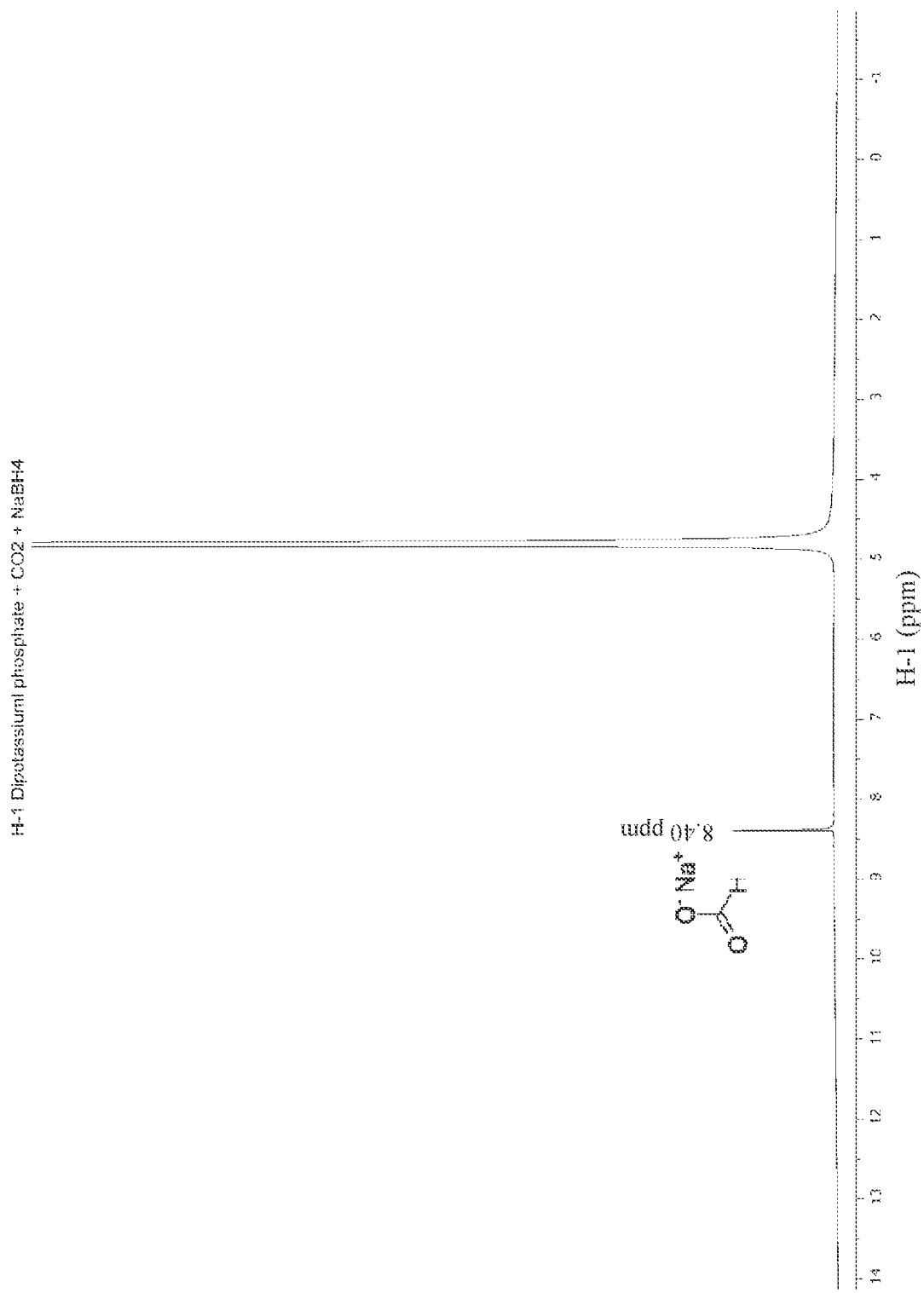
FIG. 11 shows $^1H$ nmr of dipotassium phosphate+CO2+NaBH4.
Figure 12:
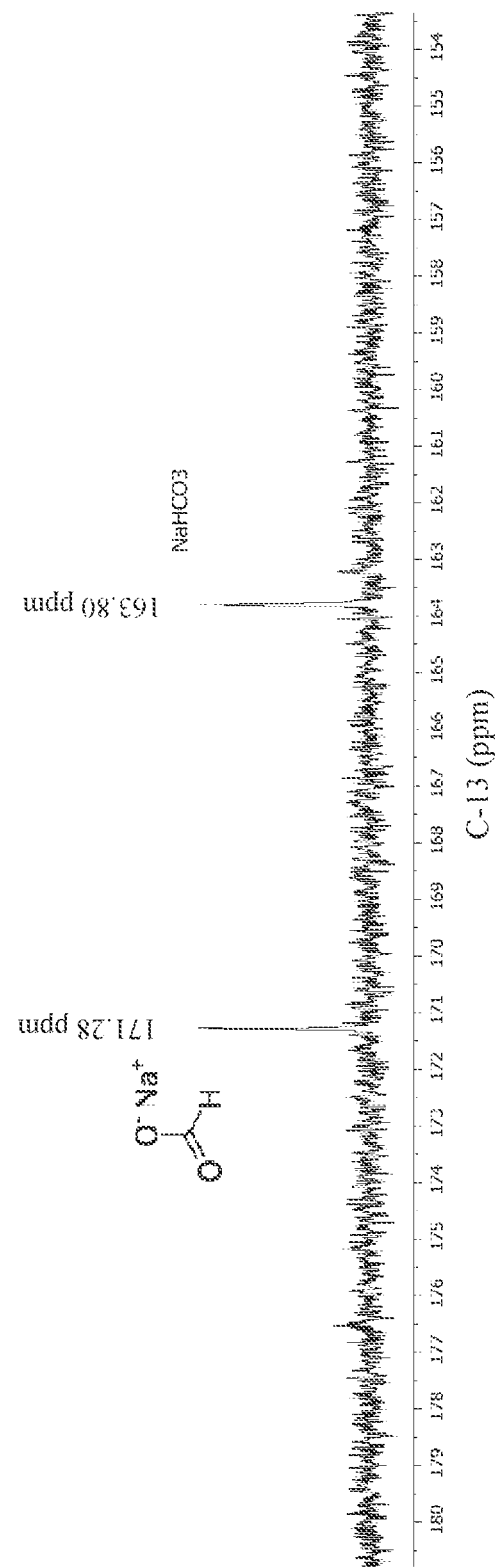
FIG. 12 shows $^{13}C$ nmr of dipotassium phosphate+CO2+NaBH4.
Figure 13:
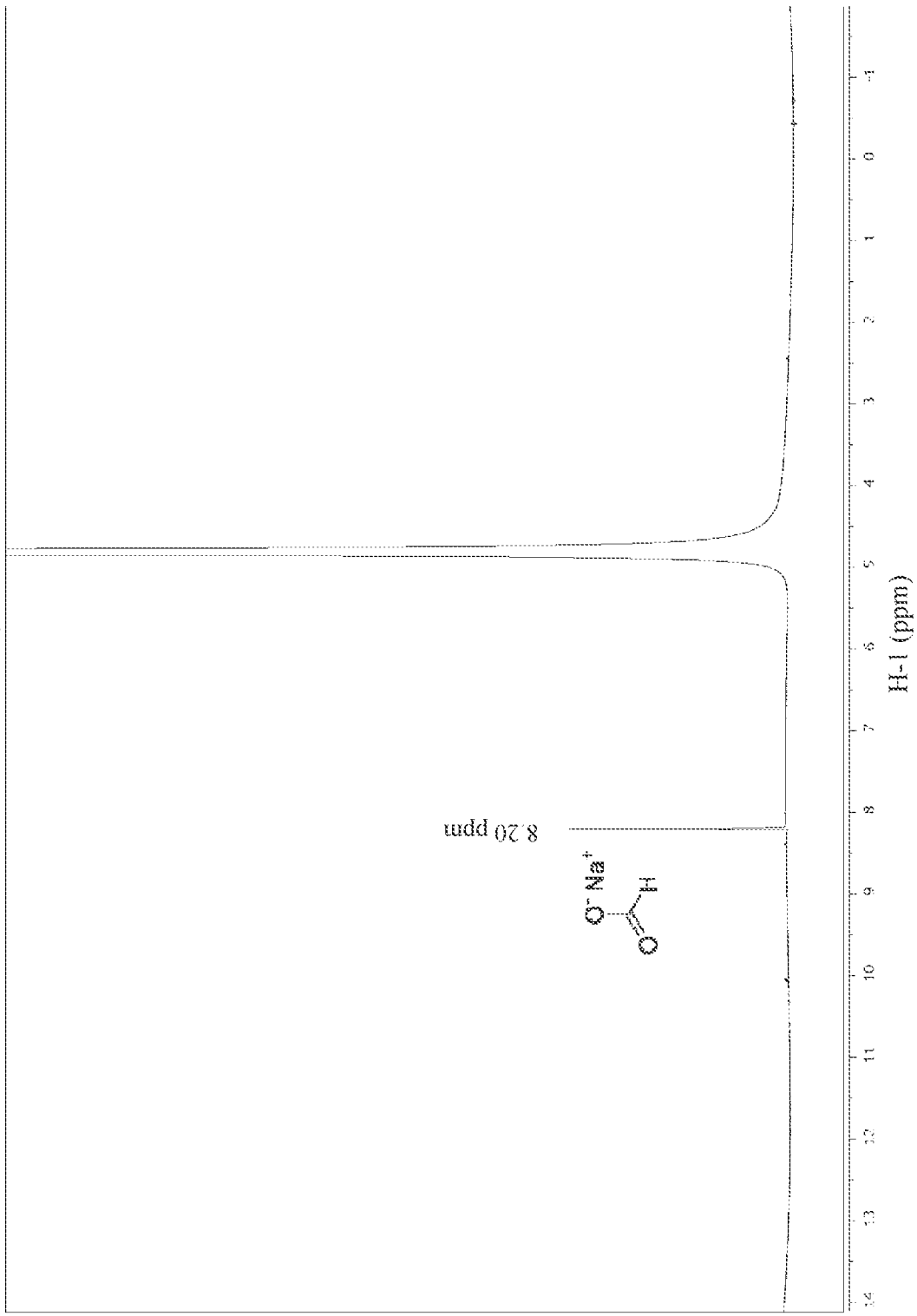
FIG. 13 shows $^1H$ nmr of dibasic ammonium phosphate+CO2+NaBH4.
Figure 14:
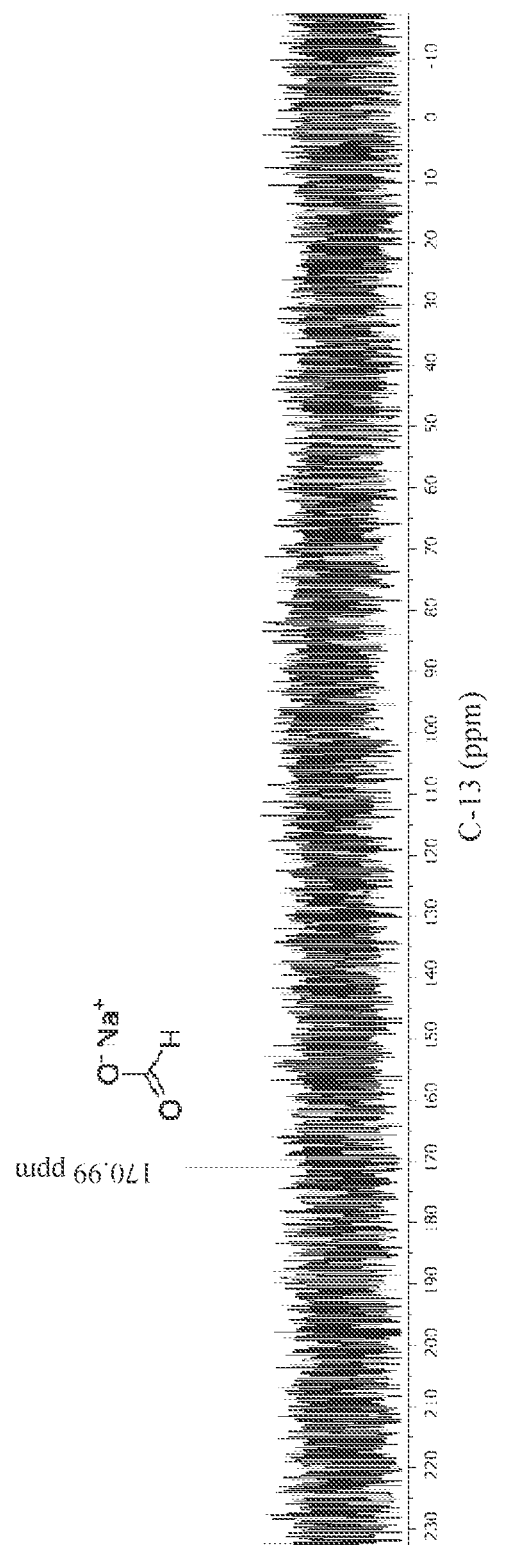
FIG. 14 shows $^{13}C$ nmr of dibasic ammonium phosphate+CO2+NaBH4.
Figure 15:
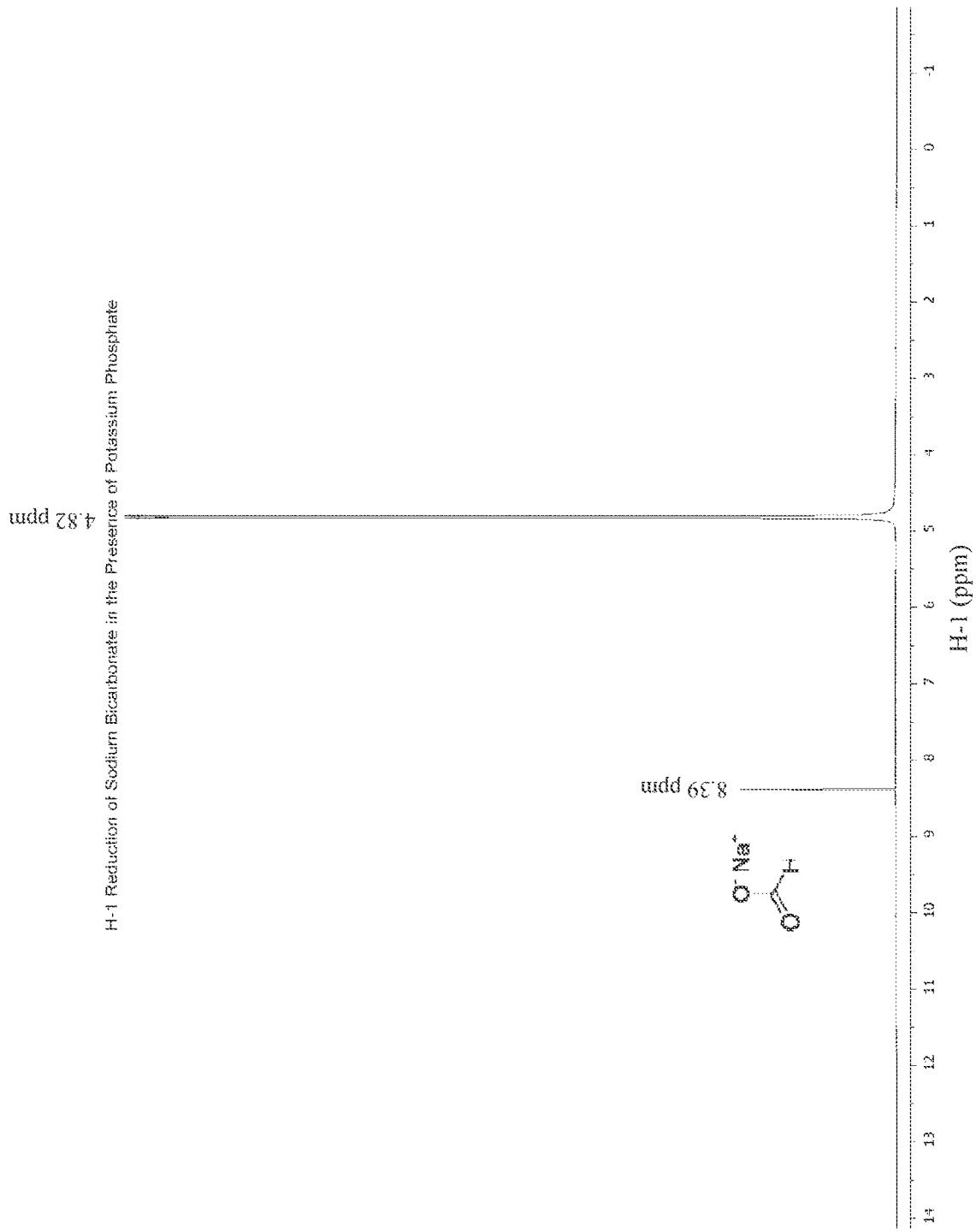
FIG. 15 shows $^1H$ nmr of sodium bicarbonate in the presence of potassium phosphate.
Figure 16:
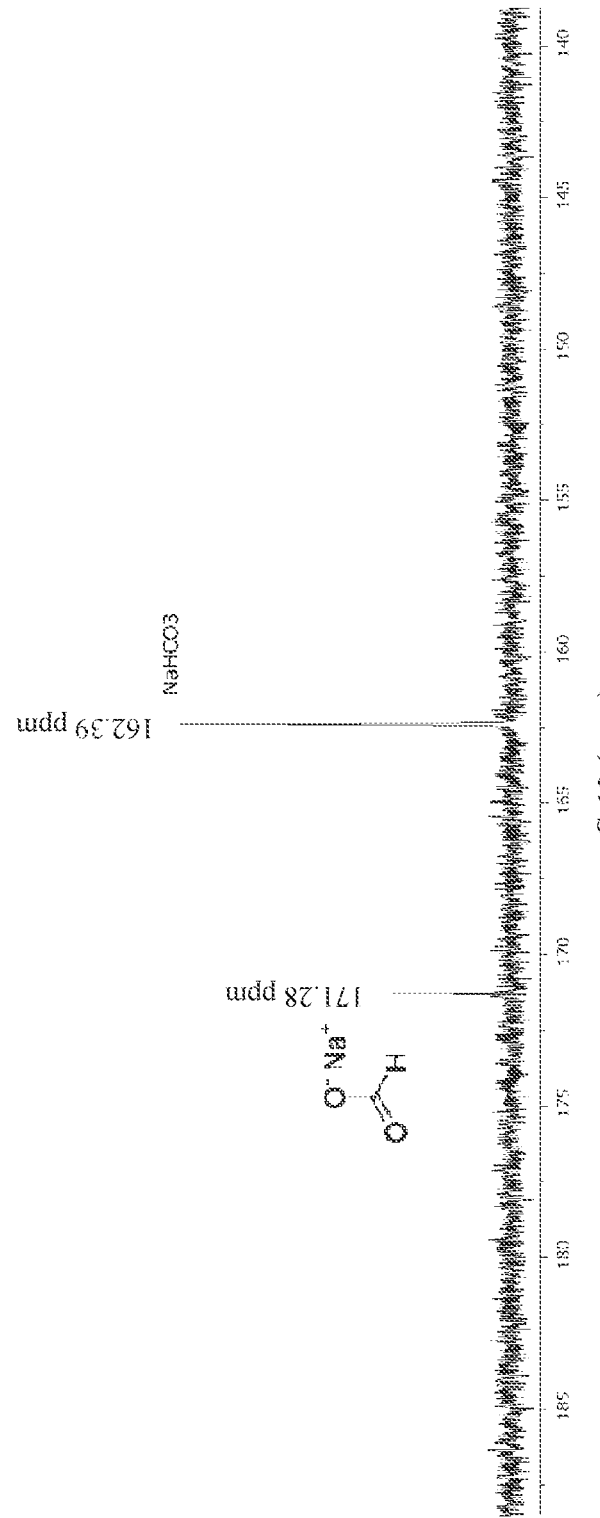
FIG. 16 shows $^{13}C$ nmr of reduction sodium bicarbonate in the presence of potassium phosphate.
Figure 17:
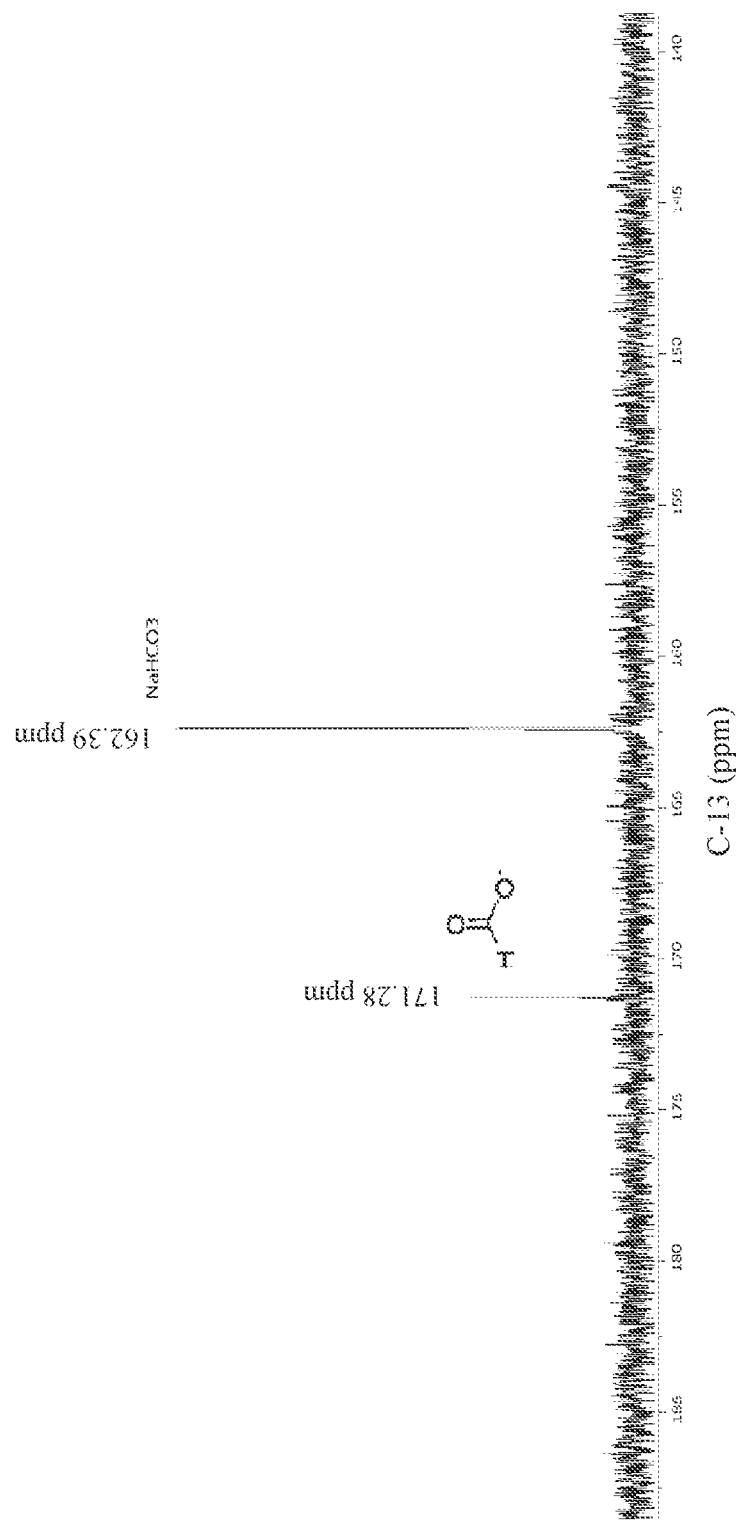
FIG. 17 shows $^{13}C$ nmr of reduction of sodium bicarbonate with sodium borohydride or the reduction of sodium carbonate with sodium borohydride in the presence of monobasic potassium phosphate.
Figure 18:
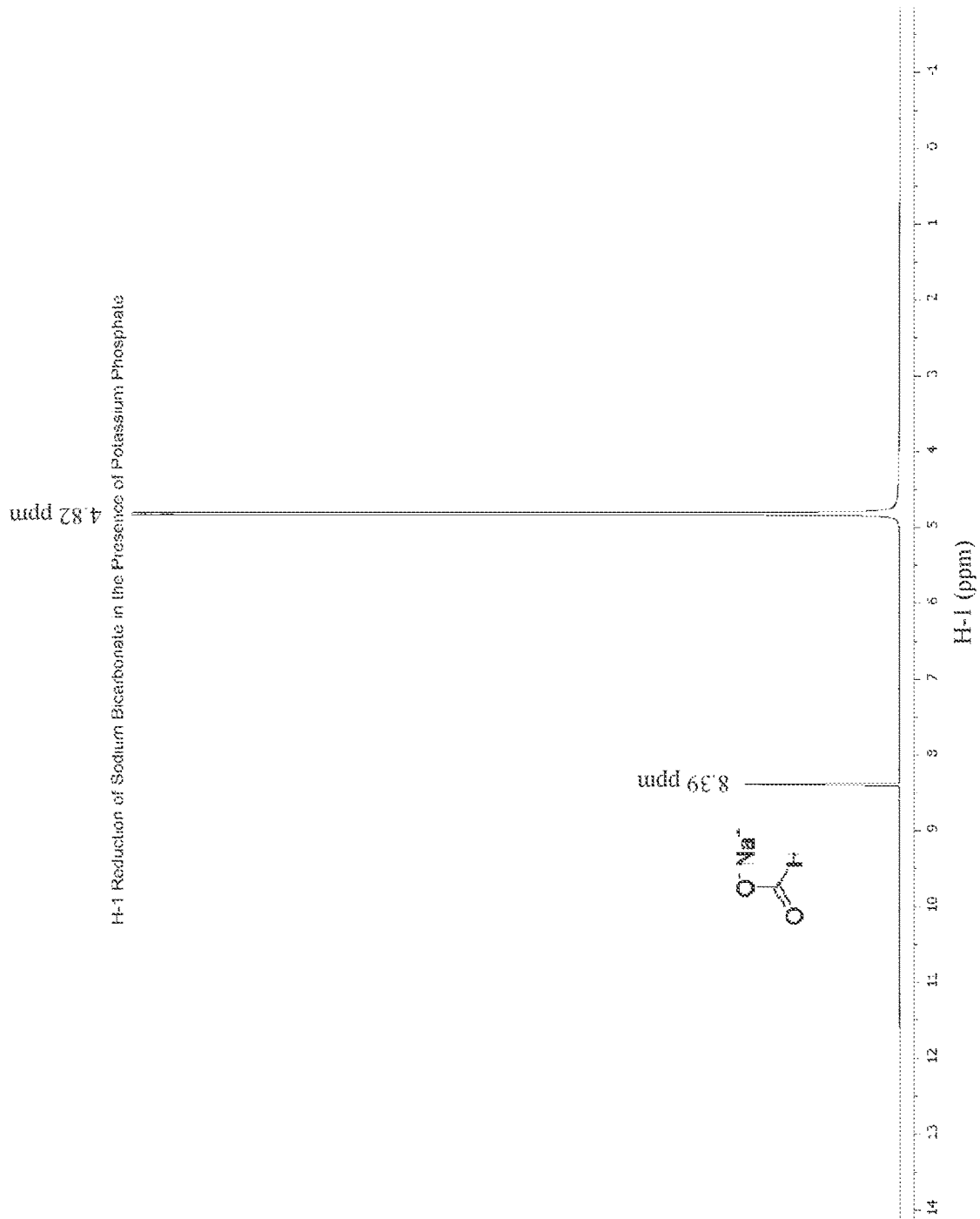
FIG. 18 shows $^1H$ nmr of reduction of sodium bicarbonate with sodium borohydride or the reduction of sodium carbonate with sodium borohydride in the presence of monobasic potassium phosphate.
Figure 19:
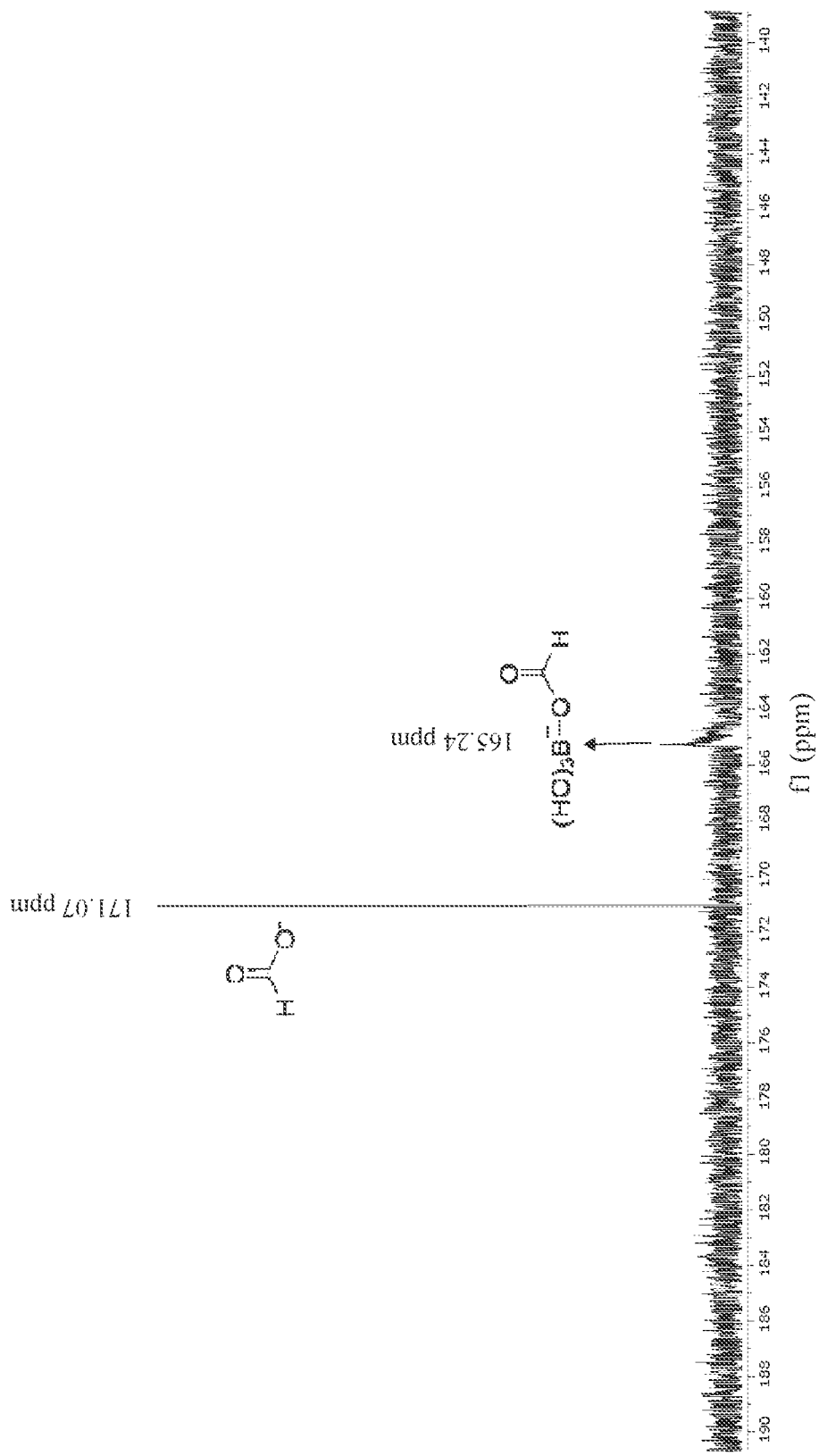
FIG. 19 shows $^{13}C$ nmr of the reduction of sodium carbonate with sodium borohydride in the presence of boric acid. The nmr shows approximately 100% conversion of the carbonate.

The presence of the formate was confirmed by HNMR chemical shift of 8.35 ppm (see FIG. 7) and a CNMR chemical shift of 171.2205 ppm (see FIG. 8).

Example 4

Reduction of Carbonates Using Sodium Borohydride and Boric Acid

A 250 mL volumetric flask containing a stirring bar was charged with a 15 mL water and 2 mmol (0.212 g) of dibasic sodium carbonate to form a solution at room temperature. To this solution, 2 mmol (0.124 g) of boric acid was added. Optionally, additional water may be added to ensure that all solid is dissolved. Advantageously, addition of sodium borohydride to the solution provides sodium formate in excellent yields. The method successfully reduced both bicarbonates and carbonates in water at room temperature and in an inexpensive manner. As shown below, observed yields were between 90-100%.

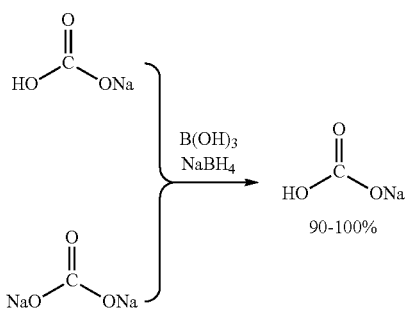

In contrast, in the absence of boric acid, sodium carbonate provided no yield of sodium formate when it was reduced. Further, when sodium carbonate was mixed with one equivalent of monobasic sodium/potassium phosphate and reduced, only a 30-40% yield of sodium formate was achieved. Similarly, 30-40% yield of the formate was achieved when sodium bicarbonate was reduced with sodium borohydride without boric acid.

The following references are hereby incorporated in their entirety into the present disclosure.

(1) Cox, P. M.; Betts, R. A.; Jones, C. D.; Spall, S. A.; Totterdell, I. J. *Nature* 2000, 408 (6809), 184-187.
(2) Leung, D. Y. C.; Caramanna, G.; Maroto-Valer, M. M. *Renew. Sustain. Energy Rev.* 2014, 39, 426-443.
(3) The Paris Agreement|UNFCCC haps://unfccc.int/process-and-meetings/the-paris-agreement/the-paris-agreement (accessed Jul. 15, 2018).
(4) Dutcher, B.; Fan, M.; Russell, A. G. *ACS Appl. Mater. Interfaces* 2015, 7 (4), 2137-2148.
(5) Ding, N.; Li, H.; Feng, X.; Wang, Q.; Wang, S.; Ma, L.; Zhou, J.; Wang, B. *J. Am. Chem. Soc.* 2016, 138 (32), 10100-10103.
(6) Mulch, G. A.; Shulda, S.; McCue, A. J.; Menart, M. J.; Ciobanu, C. V.; Ngo, C.; Anderson, J. A.; Richards, R. M.; Vega-Maza, D. *J. Am. Chem. Soc.* 2018, 140 (13), 4736-4742.
(7) Lai, Q.; Toan, S.; Assiri, M. A.; Cheng, H.; Russell, A. G.; Adidharma, H.; Radosz, M.; Fan, M. *Nat. Commun.* 2018, 9 (1), 2672.
(8) Huang, J. W.; Shi, M. *J. Org. Chem.* 2003, 68 (17), 6705-6709.
(9) Kadokawa, J.; Hideyuki, H.; Fukamachi, S.; Karasu, M.; Tagaya, H.; Chiba, K. *J. Chem. Soc. Perkin Trans. 1* 1999, 0 (15), 2205-2208.
(10) Ezhova, N. N.; Kolesnichenko, N. V.; Bulygin, A. V.; Slivinskii, E. V.; Han, S. *Russ. Chem. Bull.* 2002, 51 (12), 2165-2169.
(11) Harvey, D. J.; Struwe, W. B. *J. Am. Soc. Mass Spectrom.* 2018, 29 (6), 1179-1193.
(12) Wang, T.; Liu, F.; Ge, K.; Fang, M. *Chem. Eng. J.* 2017, 314, 123-131.
(13) Boot-Handford, M. E.; Abanades, J. C.; Anthony, E. J.; Blunt, M. J.; Brandani, S.; Mac Dowell, N.; Fernández, J. R.; Ferrari, M. C.; Gross, R.; Hallett, J. P.; Haszeldine, R. S.; Heptonstall, P.; Lyngfelt, A.; Makuch, Z.; Mangano, E.; Porter, R. T. J.; Pourkashanian, M.; Rochelle, G. T.; Shah, N.; Yao, J. G.; Fennell, P. S. *Energy Environ. Sci.* 2014, 7 (1), 130-189.
(14) Zhang, X.; Zhao, Y.; Hu, S.; Gliege, M. E.; Liu, Y.; Liu, R.; Scudiero, L.; Hu, Y.; Ha, S. *Electrochim. Acta* 2017, 247, 281-287.
(15) Froz, J.; Kalčík, J.; Cudlín, P. *Annales Zoologici Fennici*. Finnish Zoological and Botanical Publishing Board pp 269-275.
(16) Jilkova, V.; Matěhíček, L.; Frouz, J. *Eur. J. Soil Biol.* 2011, 47 (1), 72-76.
(17) Afik, O.; Delaplane, K. S.; Shafir, S.; Moo-Valle, H.; Javier, J.; Quezada-Euan, G. *J Chem Ecol* 2014, 40 (40), 476-483.
(18) Kamble, S.; Kalshetti, R.; Vaithlyanathan, V.; Sudalai, A. Metal Catalyzed Process for Reduction Of C02 To Sodium Formate And Formic Acid. WO 2016/024293 A1, 2016.
(19) Wright, Allen, B.; Lackner, Klaus, S. Method and Apparatus for Extracting Carbon Dioxide From Air. WO 2008/042919 A2, 2008. https://doi.org/Oct. 4, 2008.
(20) Chakravarti, S.; Burgers, K. L.; Gupta, A.; Williams, W. R. Carbon Dioxide Recovery From Flue Gas And The Like. WO 2007/075399 A1, 2007.
(21) Lackner, C.; Zeman, F. S. Systems And Methods For Extracting Carbon Dioxide From Air. WO 2006/009600 A2, 2006.
(22) Keith, D.; Mahmoudkhani, M. Carbon Dioxde Capture. U.S. Pat. No. 8,119,091 B2, 2012.
(23) Jones, J. D. Removing Carbon Dioxide From Waste Streams Through Co-Generation Of Carbonate and/or Bicarbonate Minerals. U.S. Pat. No. 7,727,374 B2, 2010.
(24) Grice, K. A.; Groenenboom, M. C.; Manuel, J. D. A.; Sovereign, M. A.; Keith, J. A. Examining the Selectivity of Borohydride for Carbon Dioxide and Bicarbonate Reduction in Protic Conditions. *Fuel* 2015, 150, 139-145. https://doi.org/10.1016/j.fuel.2015.02.007.

What is claimed is:

1. A method for reducing a carbonate, said method comprising the steps of:
   a. obtaining a solution comprising the carbonate;
   b. combining the carbonate of step a) with boric acid;
   c. adding sodium borohydride to the combination of step b) to reduce the carbonate to a formate.

2. The method of claim 1, wherein the method further comprises the step of stirring the combination of step b).

3. The method of claim 1, wherein the carbonate is selected from the group consisting of one or more of an ammonium carbonate, a sodium carbonate, a potassium carbonate, a rubidium carbonate, a cesium carbonate, an ammonium bicarbonate, a bisodium carbonate, a potassium bicarbonate, a rubidium bicarbonate, and a cesium bicarbonate.

4. The method of claim 1, wherein the carbonate is an alkali metal carbonate, an alkali metal bicarbonate, or a combination thereof.

5. The method of claim 1, wherein the carbonate is a sodium carbonate, a sodium bicarbonate, or a combination thereof.

6. The method of claim 1, wherein the formate is an alkali metal formate.

7. The method of claim 1, wherein the formate is a sodium formate.

8. A method for reducing a carbonate, said method comprising the steps of:
   a. dissolving the carbonate in an liquid media to form a solution;

b. combining the carbonate of step a) with boric acid;
c. adding sodium borohydride to the combination of step b) to reduce the carbonate to a formate.

9. The method of claim 8, wherein the method further comprises the step of stirring the combination of step b).

10. The method of claim 8, wherein the carbonate is selected from the group consisting of one or more of an ammonium carbonate, a sodium carbonate, a potassium carbonate, a rubidium carbonate, a cesium carbonate, an ammonium bicarbonate, a bisodium carbonate, a potassium bicarbonate, a rubidium bicarbonate, and a cesium bicarbonate.

11. The method of claim 8, wherein the carbonate is an alkali metal carbonate, an alkali metal bicarbonate, or a combination thereof.

12. The method of claim 8, wherein the carbonate is a sodium carbonate, a sodium bicarbonate, or a combination thereof.

13. The method of claim 8, wherein the formate is an alkali metal formate.

14. The method of claim 8, wherein the formate is a sodium formate.

* * * * *